United States Patent
Cho et al.

(10) Patent No.: US 9,056,157 B2
(45) Date of Patent: Jun. 16, 2015

(54) HYBRID BIODEGRADABLE/NON-BIODEGRADABLE STENT, DELIVERY SYSTEM AND METHOD OF TREATING A VASCULAR CONDITION

(75) Inventors: Junghwa Jenn Cho, San Francisco, CA (US); Joseph D. Berglund, Santa Rosa, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 1328 days.

(21) Appl. No.: 11/909,297

(22) PCT Filed: Mar. 7, 2006

(86) PCT No.: PCT/US2006/008124
§ 371 (c)(1),
(2), (4) Date: Jun. 25, 2009

(87) PCT Pub. No.: WO2006/104648
PCT Pub. Date: Oct. 5, 2006

(65) Prior Publication Data
US 2009/0306756 A1     Dec. 10, 2009

Related U.S. Application Data

(60) Provisional application No. 60/665,289, filed on Mar. 24, 2005.

(51) Int. Cl.
| | |
|---|---|
| *A61F 2/06* | (2013.01) |
| *A61L 31/14* | (2006.01) |
| *A61L 31/16* | (2006.01) |
| *A61F 2/86* | (2013.01) |

(52) U.S. Cl.
CPC ............ *A61L 31/148* (2013.01); *A61F 2/86* (2013.01); *A61L 31/16* (2013.01); *A61L 2300/00* (2013.01)

(58) Field of Classification Search
CPC ...... A61F 2/82; A61F 2/86; A61F 2210/0004
USPC ........... 623/1.11, 1.15, 1.34, 1.38, 1.42, 1.43, 623/1.44, 1.45–1.49, 1.5, 1.51–1.54, 1.12, 623/1.23, 1.13, 1.14; 606/198, 194
See application file for complete search history.

(56) References Cited

U.S. PATENT DOCUMENTS

| | | | | |
|---|---|---|---|---|
| 4,655,771 | A * | 4/1987 | Wallsten ...................... | 623/1.22 |
| 5,551,954 | A * | 9/1996 | Buscemi et al. ............. | 623/1.15 |
| 5,629,077 | A * | 5/1997 | Turnlund et al. ............. | 623/1.15 |
| 5,670,161 | A * | 9/1997 | Healy et al. .................. | 623/1.42 |
| 5,843,175 | A * | 12/1998 | Frantzen ...................... | 623/1.15 |

(Continued)

*Primary Examiner* — Katrina Stransky

(57) ABSTRACT

An intraluminal stent, an intraluminal stent delivery system, and a method of treating a vascular condition. The stent includes a framework composed of a biodegradable material. At least one strut is composed of a non-biodegradable material. The framework is operably attached to the at least one strut. The delivery system includes a catheter and a stent disposed on a portion of the catheter. The stent includes a framework composed of a biodegradable material. The stent further includes at least one strut composed of a non-biodegradable material. The framework is operably attached to the at least one strut. The method includes positioning an intraluminal stent via a catheter within a vessel. The stent includes at least one strut that is composed of a non-biodegradable material and is operably attached to a framework. The framework expands during deployment of the intraluminal stent. The framework is allowed to biodegrade within the vessel.

29 Claims, 3 Drawing Sheets

(56) References Cited

U.S. PATENT DOCUMENTS

| | | | |
|---|---|---|---|
| 5,868,782 A * | 2/1999 | Frantzen | 623/1.15 |
| 6,042,606 A * | 3/2000 | Frantzen | 623/1.18 |
| 6,245,103 B1 * | 6/2001 | Stinson | 623/1.22 |
| 6,287,332 B1 | 9/2001 | Bolz et al. | |
| 6,338,739 B1 * | 1/2002 | Datta et al. | 623/1.15 |
| 6,387,124 B1 * | 5/2002 | Buscemi et al. | 623/1.42 |
| 7,011,678 B2 * | 3/2006 | Tenerz et al. | 623/1.15 |
| 7,066,952 B2 * | 6/2006 | Igaki | 623/1.15 |
| 7,169,173 B2 * | 1/2007 | Hossainy et al. | 623/1.15 |
| 2003/0153971 A1 | 8/2003 | Chandrasekaran | |
| 2003/0195609 A1 * | 10/2003 | Berenstein et al. | 623/1.15 |
| 2004/0186556 A1 * | 9/2004 | Hogendijk et al. | 623/1.16 |
| 2005/0222671 A1 * | 10/2005 | Schaeffer et al. | 623/1.15 |

* cited by examiner

HYBRID BIODEGRADABLE/NON-BIODEGRADABLE STENT, DELIVERY SYSTEM AND METHOD OF TREATING A VASCULAR CONDITION

TECHNICAL FIELD OF THE INVENTION

The present invention relates generally to the field of implantable medical devices. More particularly, the invention relates to a hybrid biodegradable/non-biodegradable stent, delivery system, and method of treating a vascular condition.

BACKGROUND OF THE INVENTION

Balloon angioplasty is a medical procedure to widen obstructed blood vessels narrowed by plaque deposits. The procedure may be used in coronary or peripheral arteries. In an angioplasty procedure, a catheter having a special inflatable balloon on its distal end is navigated through the patient's arteries and is advanced through the artery to be treated to position the balloon within the narrowed region (stenosis). The region of the stenosis is expanded by inflating the balloon under pressure to forcibly widen the artery. After the artery has been widened, the balloon is deflated and the catheter is removed from the patient.

A significant difficulty associated with balloon angioplasty is that in a considerable number of cases the artery may again become obstructed in the same region where the balloon angioplasty had been performed. The repeat obstruction may be immediate (abrupt reclosure), which is usually caused by an intimal flap or a segment of plaque or plaque-laden tissue that loosens or breaks free as a result of the damage done to the arterial wall during the balloon angioplasty. Such abrupt reclosure may block the artery requiring emergency surgery which, if not performed immediately, may result in a myocardial infarction and, possibly, death. This risk also necessitates the presence of a surgical team ready to perform such emergency surgery when performing balloon angioplasty procedures. More commonly, a restenosis may occur at a later time, for example, two or more months after the angioplasty for reasons not fully understood and which may require repeat balloon angioplasty or bypass surgery. When such longer term restenosis occurs, it usually is more similar to the original stenosis, that is, it is in the form of cell proliferation and renewed plaque deposition in and on the arterial wall.

To reduce the incidence of re-obstruction and restenosis, several strategies have been developed. Implantable devices, such as stents, have been used to reduce the rate of angioplasty related re-obstruction and restenosis by about half. The use of such intraluminal devices has greatly improved the prognosis of these patients. The stent is placed inside the blood vessel after the angioplasty has been performed. A catheter typically is used to deliver the stent to the arterial site to be treated. The stent may further include one or more therapeutic substance(s) impregnated or coated thereon to limit re-obstruction and/or restenosis.

Numerous stent designs are known in the art. One type of stent design includes a cylindrical body formed from metallic struts. The struts form a lattice-like surface that may be rolled into a small diameter cylinder (i.e., a compressed form). The stent is positioned (e.g., compressed) onto a balloon of a catheter for subsequent deployment. It is often desirable to provide a small profile size of the stent while it is positioned onto the balloon. When positioned within the blood vessel, the balloon and stent may be expanded together. After deployment, the balloon is deflated and the metal stent is left plastically deformed and left within the vessel in an expanded form. Metallic stents are generally strong and able to withstand the shear forces present in the vasculature. Metallic stents, however, are generally not biodegradable. Therefore, metallic stents may remain within the vasculature and may have to be retrieved under certain circumstances.

Another type of stent design includes a cylindrical body formed from a tubular braided mesh of fabric (non-metallic) material. The braided mesh may be biodegradable (i.e., degrades in a controlled manner within the patient). Once the fabric stent is positioned properly, it self-expands into a larger diameter. Mesh stents can be made to be biodegradable. However, they sometimes lack sufficient mechanical strength to withstand the shear forces present in the vasculature.

Accordingly, it would be desirable to provide a hybrid biodegradable/non-biodegradable stent, delivery system, and method of treating a vascular condition that would overcome the aforementioned and other limitations.

SUMMARY OF THE INVENTION

A first aspect according to the invention provides an intraluminal stent. The stent includes a framework composed of a biodegradable material. At least one strut is composed of a non-biodegradable material. The framework is operably attached to the at least one strut.

A second aspect according to the invention provides an intraluminal stent delivery system. The delivery system includes a catheter and a stent disposed on a portion of the catheter. The stent includes a framework composed of a biodegradable material. The stent further includes at least one strut composed of a non-biodegradable material. The framework is operably attached to the at least one strut.

A third aspect according to the invention provides a method of treating a vascular condition. The method includes positioning an intraluminal stent via a catheter within a vessel. The stent includes at least one strut that is composed of a non-biodegradable material and is operably attached to a framework. The framework expands during deployment of the intraluminal stent. The framework is allowed to biodegrade within the vessel.

The foregoing and other features and advantages of the invention will become further apparent from the following description of the presently preferred embodiments, read in conjunction with the accompanying drawings. The drawings are not drawn to scale. The detailed description and drawings are merely illustrative of the invention, rather than limiting the scope of the invention being defined by the appended claims and equivalents thereof.

DESCRIPTION OF THE PRESENTLY PREFERRED EMBODIMENTS

Figure 1:
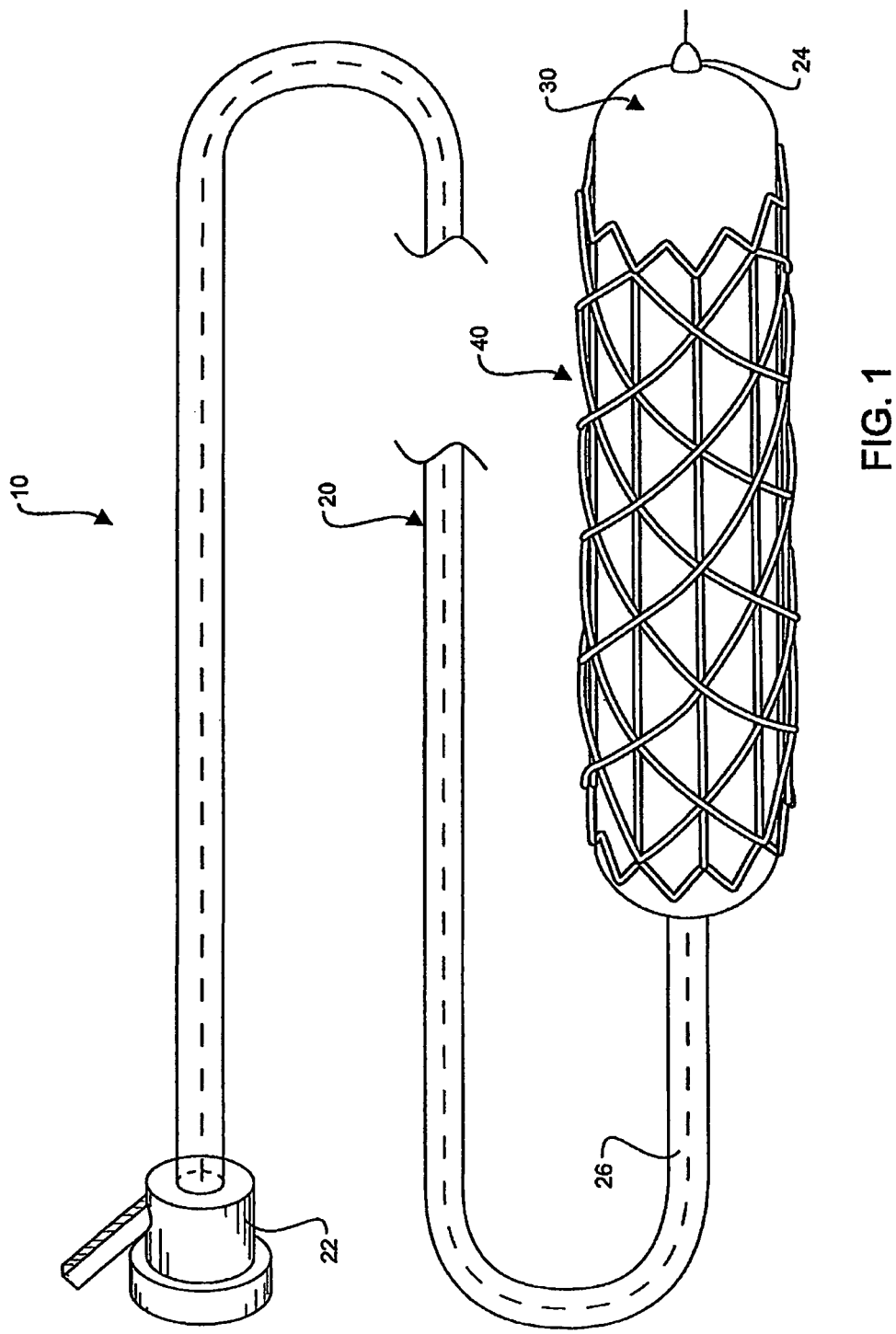
FIG. 1 is a perspective view of an intraluminal stent delivery system including a compressed stent mounted on a balloon, in accordance with one embodiment of the present invention.

Referring to the drawings, wherein like reference numerals refer to like elements, FIG. 1 is a perspective view of an intraluminal stent delivery system in accordance with one embodiment of the present invention and shown generally by numeral 10. System 10 may include a catheter 20, a balloon 30 operably attached to the catheter 20, and a stent 40 disposed on the balloon 30.

Stent 40 is shown in a compressed configuration in FIG. 1 and typically remains as such on the balloon 30 during advancement through the vasculature. The compressed stent 40 includes a relatively small profile (i.e., cross-sectional size) to minimize contact with surfaces, such as a vessel walls. Once the stent 40 is properly positioned within the vasculature, the balloon 30 and stent 40 are expanded together. Balloon 30 may then be deflated and retracted thereby allowing the stent 40 to remain in a deployed configuration. The advancement, positioning, and deployment of stents and like devices are well known in the art. In addition, those skilled in the art will recognize that numerous devices and methodologies may be adapted for deploying the stent in accordance with the present invention.

The terms "catheter" and "stent", as used herein, may include any number of intravascular and/or implantable prosthetic devices (e.g., a stent-graft); the examples provided herein are not intended to represent the entire myriad of devices that may be adapted for use with the present invention. Although the devices described herein are primarily done so in the context of deployment within a blood vessel, it should be appreciated that intravascular and/or implantable prosthetic devices in accordance with the present invention may be deployed in other vessels, such as a bile duct, intestinal tract, esophagus, airway, etc. Further, the terms "biodegradable" and "non-biodegradable", as used herein, refer to a relative stabilities of substances when positioned within a living being. For example, a biodegradable substance will decay (i.e., break down) at a faster rate than a non-biodegradable substance. A non-biodegradable substance, however, may, eventually decay given a sufficient amount of time.

Catheter 20 may comprise an elongated tubular member manufactured from one or more polymeric materials, sometimes in combination with metallic reinforcement. In some applications (such as smaller, more tortuous arteries), it is desirable to construct the catheter from very flexible materials to facilitate advancement into intricate access locations. Numerous over-the-wire, rapid-exchange, and other catheter designs are known and may be adapted for use with the present invention. Catheter 20 may be secured at its proximal end to a suitable Luer fitting 22, and may include a distal rounded end 24 to reduce harmful contact with a vessel. Catheter 20 may be manufactured from a material such as a thermoplastic elastomer, urethane, polymer, polypropylene, plastic, ethelene chlorotrifluoroethylene (ECTFE), polytetrafluoroethylene (PTFE), fluorinated ethylene propylene copolymer (FEP), nylon, Pebax® resin, Vestamid® nylon, Tecoflex® resin, Halar® resin, Hyflon® resin, Pellathane® resin, combinations thereof, and the like. Catheter 20 may include an aperture formed at the distal rounded end 24 allowing advancement over a guidewire 26.

Balloon 30 may be any variety of balloons or other devices capable of expanding the stent 40 (e.g., by providing outward radial forces). Balloon 30 may be manufactured from any sufficiently elastic material such as polyethylene, polyethylene terephthalate (PET), nylon, or the like. Those skilled in the art will recognize that the stent 40 may be expanded using a variety of means and that the present invention is not limited strictly to balloon expansion.

Figure 2:
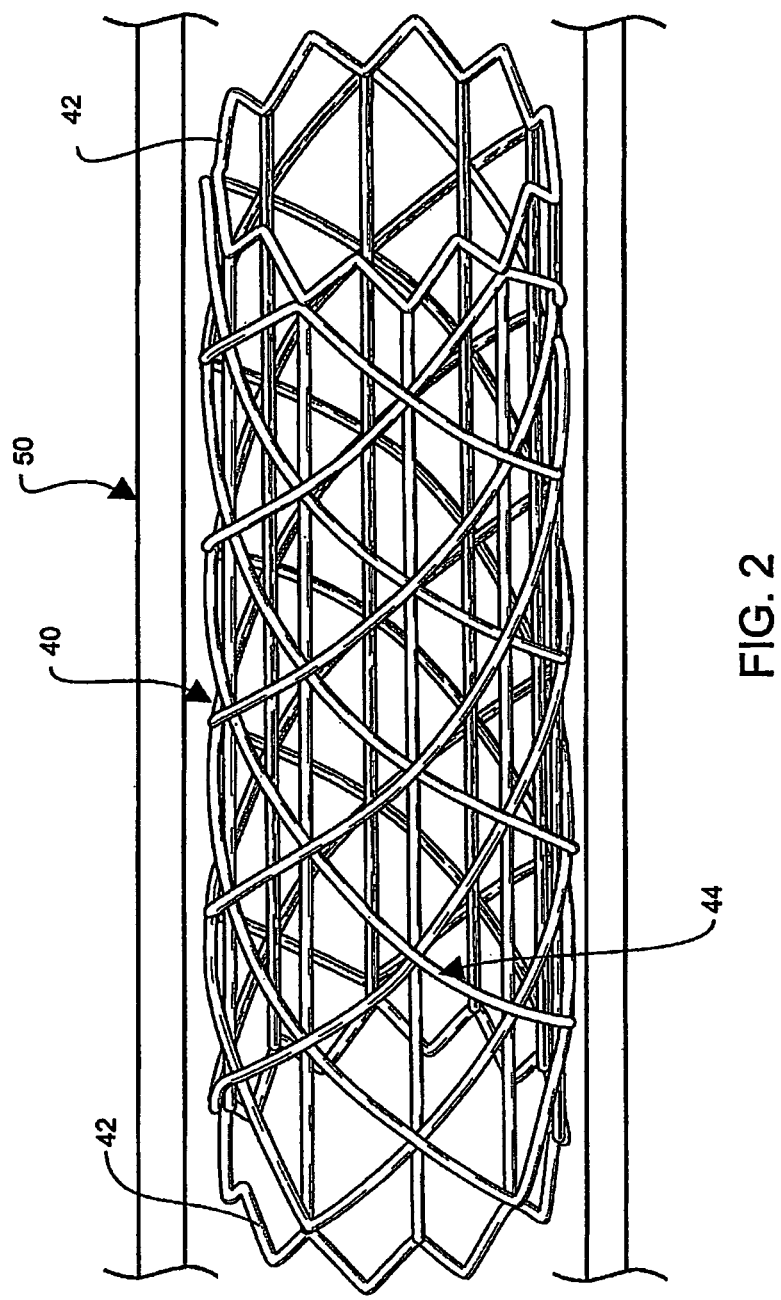
FIG. 2 is a perspective view the stent of FIG. 1, the stent shown in an deployed configuration and positioned within a vessel, in accordance with one embodiment of the present invention.

FIG. 2 is a detailed view of the stent 40 shown in a deployed configuration within a vessel 50. In one embodiment, the stent 40 may include a generally tubular body defining a passageway extending along a longitudinal axis. Stent 40 includes at least one, and in this case two, struts 42 composed of at least one non-biodegradable material. Struts 42 are preferably manufactured from an inert, biocompatible material with high corrosion resistance and that is deformed to and maintained at the expanded stent diameter at low to moderate stress levels. Struts 42 may enhance stent 40 visualization (to aid deployment), radial strength, and help to maintain vascular patency. Further, the enhanced stent 40 visualization may also be used to assist in patient follow-up procedures. Suitable materials for the struts 42 include, but are not limited to, a metal, a ceramic, a polymer, tantalum, stainless steel, titanium ASTM F63-83 Grade 1, niobium, high carat gold K 19-22, MP35N, and combinations thereof. In one embodiment, the struts 42 may be entirely manufactured from a non-biodegradable material. In another embodiment, the struts 42 may be manufactured from both a non-biodegradable (e.g., about 10 percent or greater) and a biodegradable material so that a portion thereof is degraded over time.

Stent 40 further includes a biodegradable framework 44 operably attached to the struts 42. In one embodiment, the struts 42 are bonded to the framework 44 using adhesive(s), weld(s), or other attachment means known in the art. Framework 44 is preferably manufactured from a biocompatible material that provides adequate strength (e.g., to overcome blood-flow shear forces). Suitable materials for the framework 44 include, but are not limited to, a ceramic, a polymer, and combinations thereof. Framework 44 may span the distance between the struts 42 as braided fibers, cut tubes, straight spans, and the like.

Figures 3A, 3B:
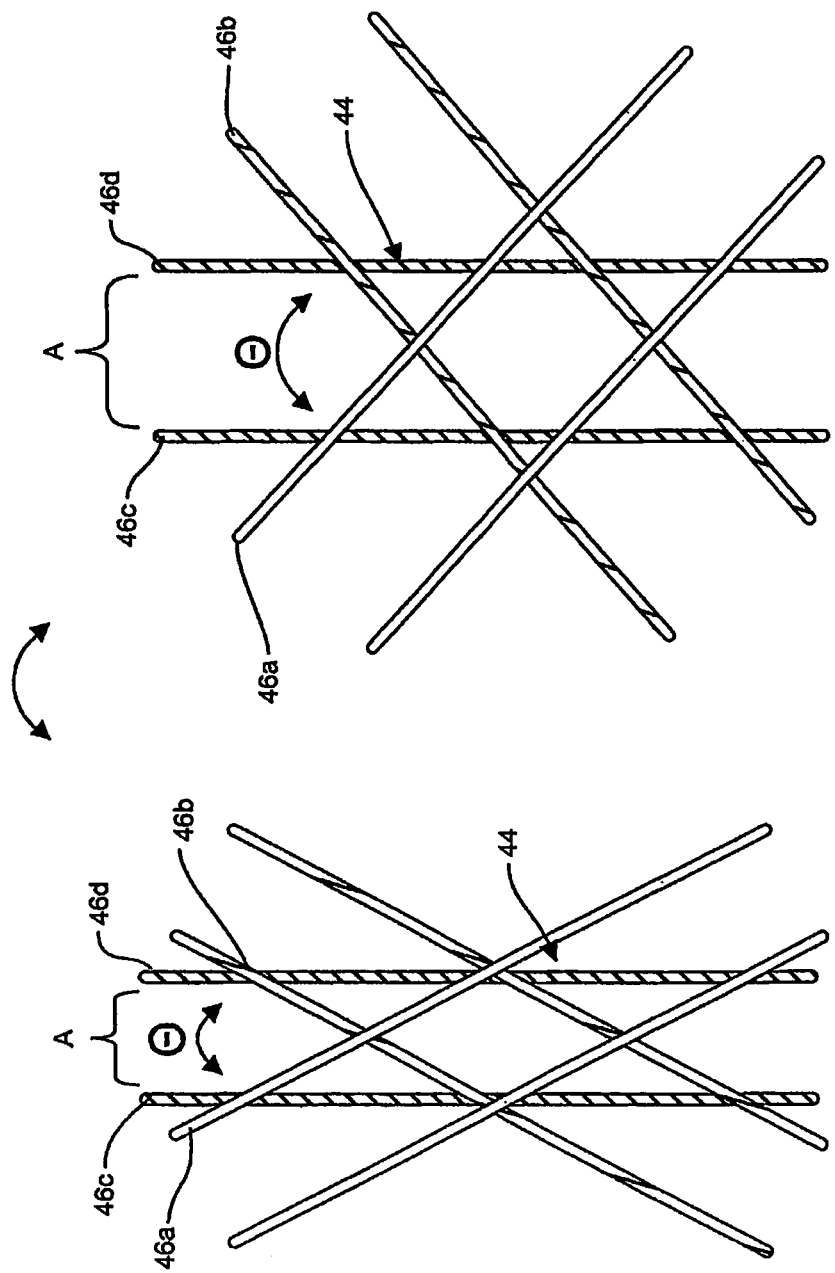
FIGS. 3A and 3B illustrate framework fibers of a compressed stent and a deployed stent, respectively, in accordance with one embodiment of the present invention.

In one embodiment, the framework 44 may be woven in a number of structural shapes that facilitates reconfiguration during deployment of the stent 40. As shown in FIGS. 3A and 3B, the framework 44 may be a three-way weaving pattern (i.e., three sets of paired interwoven fibers). Such weaves may provide a relatively high radial strength to the stent 40. During stent 40 deployment, balloon expansion results in expansion of the framework 44. Specifically, the expansion may include an increase in angle, $\theta$, between curved helical fibers 46a, 46b relative to one another as the framework 44 expands. The expansion may further include an increase in spacing A between straight longitudinal fibers 46c, 46d relative to one another and/or sliding of the fibers 46b, 46d relative to one another. In another embodiment, the framework may be formed from a structural braid, knit, mesh, and the like, and/or another weave (e.g., a two-way weave). The inventors contemplate a myriad of framework shapes and constitutions in accordance with the present invention.

In one embodiment, the stent 40 may include at least one therapeutic agent as part of one or more coatings. The coatings may be positioned on various portions of the struts 42 and framework 44. For example, one or more therapeutic agents may be positioned on the fibers 46a, 46b of the framework 44. As such, the agent(s) may be delivered to the vascular endothelium as the framework 44 biodegrades. The therapeutic agent coating may comprise one or more drugs, polymers, and the like. For example, the therapeutic agent coating may include a mixture of a drug and a polymer. The drug and polymer mixture is dissolved in a compatible liquid solvent, as known in the art, forming a solution suitable for applying to the stent framework. Some exemplary drug classes that may be included are antiangiogenesis agents, antiendothelin agents, anti-inflammatory agents, antimitogenic factors, antioxidants, antiplatelet agents, antiproliferative agents, antisense oligonucleotides, antithrombogenic agents, calcium channel blockers, clot dissolving enzymes, growth factors, growth factor inhibitors, nitrates, nitric oxide releasing agents, vasodilators, virus-mediated gene transfer agents, agents having a desirable therapeutic application, and the like.

Those skilled in the art will recognize that the nature of the drugs and polymers may vary greatly and are typically formulated to achieve a given therapeutic effect, such as limiting restenosis, thrombus formation, hyperplasia, etc. Once formulated, a therapeutic agent (mixture) comprising the coating(s) may be applied to the stent by any of numerous strategies known in the art including, but not limited to, spraying, dipping, rolling, nozzle injection, and the like. It will be recognized that the at least one therapeutic agent coating may be alternatively layered, arranged, configured on/within the stent depending on the desired effect. Before application, one or more primers may be applied to the stent to facilitate adhesion of the at least one therapeutic agent coating. Once the at least one therapeutic agent coating solution is/are applied, it/they may be dried (i.e., by allowing the solvent to evaporate) and, optionally, other coating(s) (e.g., a "cap" coat) added thereon. Numerous strategies of applying the primer(s), therapeutic agent coating(s), and cap coat(s) in accordance with the present invention are known in the art.

Upon reading the specification and reviewing the drawings hereof, it will become immediately obvious to those skilled in the art that myriad other embodiments of the present invention are possible, and that such embodiments are contemplated and fall within the scope of the presently claimed invention. The scope of the invention is indicated in the appended claims, and all changes that come within the meaning and range of equivalents are intended to be embraced therein.

While the embodiments of the invention disclosed herein are presently considered to be preferred, various changes and modifications can be made without departing from the spirit and scope of the invention. For example, the intraluminal device is not limited to any particular design, such as a stent. In addition, the strut(s), framework, and their configuration may be varied while providing a functional hybrid biodegradable/non-biodegradable intraluminal device.

The invention claimed is:

1. An intraluminal stent having a first end and a second end, the intraluminal stent comprising:
   a framework comprising straight longitudinal fibers and curved helical fibers, the framework consisting essentially of biodegradable material; and
   a first non-biodegradable strut located at the first end of the intraluminal stent and a second non-biodegradable strut located at the second end of the intraluminal stent;
   wherein each of the straight longitudinal fibers and each of the curved helical fibers is operably attached to the first non-biodegradable strut and the second non-biodegradable strut, and wherein the straight longitudinal fibers extend continuously from the first non-biodegradable strut to the second non-biodegradable strut such that the straight longitudinal fibers and the first and second non-biodegradable struts define a tubular body extending from the first end to the second end of the intraluminal stent, and wherein the curved helical fibers extend continuously around an exterior of the tubular body from the first non-biodegradable strut to the second non-biodegradable strut.

2. The stent of claim 1 wherein the non-biodegradable material is chosen from a group consisting of plastically deformable material and super-elastically self-expandable material.

3. The stent of claim 1 wherein at least one of the first and second non-biodegradable struts is radiopaque.

4. The stent of claim 1 wherein at least one of the first and second non-biodegradable struts comprises a structural support.

5. The stent of claim 1 wherein at least one of the first and second non-biodegradable struts comprises a crown shape.

6. The stent of claim 1 wherein at least one therapeutic agent is positioned on a portion of the stent.

7. The stent of claim 1 wherein the framework comprises at least one of a braided pattern, a knitted pattern, a mesh pattern, and a weaving pattern.

8. The stent of claim 1 wherein the framework expands during a stent deployment.

9. The stent of claim 1 wherein the intraluminal stent includes only one non-biodegradable strut at the first end and only one non-biodegradable strut at the second end.

10. The stent of claim 1 wherein:
    adjacent straight longitudinal fibers are separated by a first distance in a compressed configuration of the stent and by a second distance in a deployed configuration of the stent, the second distance being greater than the first distance; and
    overlapping curved helical fibers are positioned at a first angle opening towards the first end in the compressed configuration and at a second angle opening towards the first end in the deployed configuration, the second angle being greater than the first angle.

11. The stent of claim 1 wherein the straight longitudinal fibers have a fixed length during deployment and use.

12. The stent of claim 1 wherein the straight longitudinal fibers are directly attached to the first non-biodegradable strut and the second non-biodegradable strut.

13. An intraluminal stent delivery system comprising:
    a catheter; and
    a stent having a first end and a second end disposed on a portion of the catheter, the stent including a framework, a first non-biodegradable strut located at the first end of the stent and a second non-biodegradable strut located at the second end of the stent, the framework comprising straight longitudinal fibers and curved helical fibers, the framework consisting essentially of biodegradable material;
    wherein each of the straight longitudinal fibers and each of the curved helical fibers is operably attached to the first non-biodegradable strut and the second non-biodegradable strut, and wherein the straight longitudinal fibers extend continuously from the first non-biodegradable strut to the second non-biodegradable strut such that the straight longitudinal fibers and the first and second non-biodegradable struts define a tubular body extending from the first end to the second end of the stent, and wherein the curved helical fibers extend continuously around an exterior of the tubular body from the first non-biodegradable strut to the second non-biodegradable strut.

14. The system of claim 13 wherein the non-biodegradable material is chosen from a group consisting of plastically deformable material and super-elastically self-expandable material.

15. The system of claim 13 wherein at least one of the first and second non-biodegradable struts is radiopaque.

16. The system of claim 13 wherein at least one of the first and second non-biodegradable struts comprises a structural support.

17. The system of claim 13 wherein at least one of the first and second non-biodegradable struts comprises a crown shape.

18. The system of claim 13 wherein at least one therapeutic agent is positioned on a portion of the stent.

19. The system of claim 13 wherein the framework comprises at least one of a braided pattern, a knitted pattern, a mesh pattern, and a weaving pattern.

20. The system of claim 13 wherein the framework expands during a stent deployment.

21. The system of claim 13 wherein the stent includes only one non-biodegradable strut at the first end and only one non-biodegradable strut at the second end.

22. The delivery system of claim 13 wherein the straight longitudinal fibers have a fixed length during deployment and use.

23. The system of claim 13 wherein the straight longitudinal fibers are directly attached to the first non-biodegradable strut and the second non-biodegradable strut.

24. A method of treating a vascular condition, the method comprising:
  positioning an intraluminal stent having a first end and a second end via a catheter within a vessel, the intraluminal stent having a biodegradable framework comprising straight longitudinal fibers and curved helical fibers, the biodegradable framework consisting essentially of biodegradable material, a first non-biodegradable strut located at the first end of the intraluminal stent and a second non-biodegradable strut located at the second end of the intraluminal stent, wherein each of the straight longitudinal fibers and each of the curved helical fibers is operably attached to the first non-biodegradable strut and the second non-biodegradable strut, and wherein the straight longitudinal fibers extend continuously from the first non-biodegradable strut to the second non-biodegradable strut such that the straight longitudinal fibers and the first and second non-biodegradable struts define a tubular body extending from the first end to the second end of the intraluminal stent, and wherein the curved helical fibers extend continuously around an exterior of the tubular body from the first non-biodegradable strut to the second non-biodegradable strut;
  expanding the biodegradable framework during deployment of the intraluminal stent;
  allowing the biodegradable framework to biodegrade within the vessel.

25. The method of claim 24 wherein the expanding the biodegradable framework includes sliding of the straight longitudinal fibers and the curved helical fibers relative to one another.

26. The method of claim 24 further comprising eluting at least one therapeutic agent from the stent.

27. The method of claim 24 wherein the intraluminal stent includes only one non-biodegradable strut at the first end and only one non-biodegradable strut at the second end.

28. The method of claim 24 wherein the straight longitudinal fibers have a fixed length during deployment and use.

29. The method of claim 24 wherein the straight longitudinal fibers are directly attached to the first non-biodegradable strut and the second non-biodegradable strut.

* * * * *